United States Patent
Pecher et al.

(10) Patent No.: US 9,474,711 B2
(45) Date of Patent: Oct. 25, 2016

(54) **EXTRACT OF *KNIPHOFIA UVARIA* SEEDS, COSMETIC OR DERMATOLOGICAL COMPOSITION CONTAINING SAME, AND USES THEREOF**

(71) Applicant: LVMH RECHERCHE, Saint Jean de Braye (FR)

(72) Inventors: Virginie Pecher, La Chapelle Saint Mesmin (FR); Virginie Leplanquais, Donnery (FR); Anne-Sophie Colin, Saint Jean de Braye (FR); Jocelyne Franchi, Saint Jean de la Ruelle (FR); Isabelle Renimel, Trainou (FR); Kristell Lazou, Orleans (FR)

(73) Assignee: LVMH RECHERCHE, Saint Jean de Braye (FR)

( * ) Notice: Subject to any disclaimer, the term of this patent is extended or adjusted under 35 U.S.C. 154(b) by 67 days.

(21) Appl. No.: 14/370,163

(22) PCT Filed: Jan. 2, 2013

(86) PCT No.: PCT/FR2013/050001
§ 371 (c)(1),
(2) Date: Jul. 1, 2014

(87) PCT Pub. No.: WO2013/102727
PCT Pub. Date: Jul. 11, 2013

(65) Prior Publication Data
US 2015/0004267 A1 Jan. 1, 2015

(30) Foreign Application Priority Data
Jan. 4, 2012 (FR) ..................................... 12 50077

(51) Int. Cl.
| | | |
|---|---|---|
| *A61K 8/97* | (2006.01) | |
| *A61K 36/896* | (2006.01) | |
| *A61Q 19/00* | (2006.01) | |
| *A61Q 19/08* | (2006.01) | |
| *A61K 8/92* | (2006.01) | |
| *A61K 36/88* | (2006.01) | |

(52) U.S. Cl.
CPC .................. *A61K 8/97* (2013.01); *A61K 8/922* (2013.01); *A61K 36/88* (2013.01); *A61K 36/896* (2013.01); *A61Q 19/00* (2013.01); *A61Q 19/004* (2013.01); *A61Q 19/007* (2013.01); *A61Q 19/08* (2013.01); *A61K 2800/10* (2013.01)

(58) Field of Classification Search
None
See application file for complete search history.

(56) References Cited

PUBLICATIONS

Boross (Acta Chim. Hung Tomus (1963), vol. 35, pp. 195-198).*
Tandon, S. (2008) Decoction and Hot Continuous Extraction Techniques. In S.S. Handa et al. (Eds.), Extraction Technologies for Medicinal and Aromatic Plants (pp. 93-106). Trieste, Italy: ICS-UNIDO.*
Bertucco, A. ((2008) Supercritical Fluid Extraction of Medicinal and Aromatic Plants: Fundamentals and Applications. In S.S. Handa et al. (Eds.), Extraction Technologies for Medicinal and Aromatic Plants (pp. 93-106). Trieste, Italy: ICS-UNIDO).*
L. Boross: "Isolation and Identification of the Antibacterial Substance of Kniphofia uvaria"; ACTA Chimica Academiae Scientiarum Hungarica, Budapest, HU, vol. 35, Jan. 1963, pp. 195-198.
E.H. Lucas et al.: "The Occurrence O Antibacterial Substances in Seed Plants With Special Reference to Mycobacterium Tuberculosis"; Bulletin of the Torrey Botanical Club; vol. 78, No. 4, Jul. 1951, pp. 310-321.
Anonymous: "Perfums Christian Dior Press File April 2009": Feb. 2009, http://www.tfwa.com/duty_free/fileadmin/user_upload/ap/090313_dior.pdf, XP-002676771 (46 pages).
Anonymous: "Satin Revitalizing Creme"; Database GNPD [online] Miintel, Jun. 2011, www.gnpd.com, XP-002676772 (6 pages).
L. Ferenczy: "Antibacterial substances in seeds"; Nature: International Weekly Journal of Science, Nature Publishing Group, UK, vol. 178, No. 4534, Sep. 1956, pp. 639-640.
M. Schmuth et al.: "Peroxisome proliferator-activated receptors and liver X receptors in epidermal biology"; Journal of Lipid Research, http://www.jlr.org, vol. 49, 2008, pp. 499-509.
M. Man et al.: "Deficienty of PPAB$\beta/\delta$ in the Epidermis Results in Defective Cutaneous Permeability Barrier Homeostasis and Increased Inflammation"; Journal of Investigative Dermatology, 2008, vol. 128, pp. 370-377.
L. Piqueras et al.: "Activation of PPAB$\beta/\delta$ inhibits leukocyte recruitment, cell adhesion molecule expression, and chemokine release"; Journal of Leukocyte Biology, vol. 86, Jul. 2009, pp. 115-122.
A. Freund et al.: "Inflammatory Networks during Cellular Senescence: Causes and Consequences"; Trend Mol Med., May 2010, 16(5), pp. 238-246.
International Search Report, Mar. 12, 2013; PCT/FR2013/050001 (submitted Jul. 1, 2014).

* cited by examiner

*Primary Examiner* — Susan Hoffman
(74) *Attorney, Agent, or Firm* — Hamre, Schumann, Mueller & Larson, P.C.

(57) ABSTRACT

An extract of the seeds of the *Kniphofia uvaria* plant is obtained by bringing into contact with at least one cosmetically acceptable nonpolar solvent, for example, $CO_2$, under supercritical conditions, or by mechanical pressing. This disclosure also relates to a cosmetic or dermatological composition comprising said extract. This disclosure also relates to a cosmetic or dermatological care method comprising the application of said composition for preventing or delaying the appearance of the signs of skin aging, modulating the reactivity of sensitive skin, or maintaining the barrier function of the skin.

6 Claims, No Drawings

EXTRACT OF *KNIPHOFIA UVARIA* SEEDS, COSMETIC OR DERMATOLOGICAL COMPOSITION CONTAINING SAME, AND USES THEREOF

The invention relates to an extract of the seeds of the *Kniphofia uvaria* plant, to a cosmetic or dermatological composition comprising said extract and to the use thereof, in particular as an anti-aging agent or an anti-inflammatory agent.

PRIOR ART

The *Kniphofia uvaria* plant is a rhizomatous perennial species of the family Liliacea (conventional classification) and Asphodelaceae (phylogenetic classification). This hardy species has narrow hanging leaves, which can reach a meter in length. The influorescences form a spike composed of numerous tubular flowers having flamboyant colors.

For two months of the year, the flowers produce a large amount of nectar, which contains essentially water, amino acids, glucose, fructose, mineral salts and trace elements. This nectar therefore contains all the basic elements required for cell nutrition, but it also contains superoxide dismutase, an enzyme which combats lipoperoxidation caused by free radicals.

Given its composition, the nectar of *Kniphofia uvaria* flowers is particularly suitable for dry skin care in order to deeply nourish and revitalize said skin, and it has already been incorporated into a regenerating and revitalizing cosmetic care product. It has also been proposed in another cosmetic care product in combination with anti-aging active agents, the action of which it supplements.

The applicant has demonstrated, entirely surprisingly, that an extract of seeds of the *Kniphofia uvaria* plant itself has anti-aging activity, so that it is not necessary to add another anti-aging active agent to this particular extract in order to provide a care product for combating skin aging.

To date, no extraction process using the seeds of the *Kniphofia uvaria* plant has been described. It is therefore particularly surprising to have demonstrated that such an extract exhibits cosmetic activity.

The inventors of the present invention have thus first of all demonstrated that an extract of seeds of the *Kniphofia uvaria* plant, in particular a lipophilic extract of these seeds, reduces the production of pro-Matrix MetalloProteinase type 1 (pro-MMP1), a key enzyme responsible for extracellular matrix degradation, which degradation is particularly accelerated by UV radiation.

It has likewise been shown that in vitro treatment of fibroblasts with the extract of the invention causes a strong inhibition of the expression of metalloproteinases, more particularly MMP-2 and MMP-9, which are enzymes responsible for the degradation of extracellular matrix proteins.

It has also been demonstrated that an extract of the invention is an agonist of peroxisome proliferator-activated receptors (PPARs), a β/δ isotope of which is predominant in the epidermis. This interaction between the agonist and the PPAR receptor causes the activation of the transcription of target genes, in particular involved in keratinocyte differentiation. This process thus results in the formation of the stratum corneum, in particular by stimulating the synthesis of epidermal lipids, by increasing the formation and secretion of lamellar bodies or else by increasing the activity of enzymes involved in the mechanism of extracellular secretion of lipids in the horny layer (Schmuth M. et al., J. Lipids Res., 2008, 49, 499-509).

PPARs are also known for their anti-inflammatory activity (Man M. et al. 2008, J. Invest. Dermatol., 128, 370-377), by targeting in particular neutrophil-endothelial cell interactions (Piqueras L. et al. 2009, J. Leucocyte Biol., 86, 115-122).

Moreover, the micro-inflammatory status (or the notion of sterile inflammation) of aged tissues is increasingly recognized, the pro-inflammatory phenotype of senescent cells disrupting tissue homeostasis. MMPs are among the factors secreted by senescent cells as a source of chronic inflammation that is harmful to the surrounding cells and the tissue (Freund A. et al., 2010, Trends Mol. Med., 16, 238-246).

Finally, it has been shown by the inventors that this extract possesses the property of modulating the expression of genes encoding certain proteins involved in several biological processes associated with skin aging, with the hydration state of the skin and of the tissues, or else with the level of firmness and/or of elasticity of the skin.

By virtue of its activity with respect to these targets, such an extract is of interest for use as an active agent in cosmetic or dermatological compositions, in particular intended for combating skin aging, for contributing to maintaining the firmness and/or for maintaining the barrier function of the skin.

Moreover, when the extract according to the invention has an oily consistency, it is particularly advantageous to use it as a cosmetic excipient, more particularly as a texturing agent of fatty phases of cosmetic compositions.

PURPOSES OF THE INVENTION

The principal purpose of the invention is to provide a novel extract of plant origin, in particular which can be used as an active agent and/or excipient in cosmetic or dermatological compositions, in particular intended for preventing or delaying the appearance of the signs of skin aging or for slowing down or reducing the effects.

The purpose of the invention is also to provide a novel extract of plant origin for combating the effects induced by the exposure of skin cells to UV radiation, such as extracellular matrix degradation and/or the taking hold of an ultimately detrimental micro-inflammatory status, or else to contribute to maintaining the firmness and/or the barrier function of the skin.

The purpose of the invention is also to provide a cosmetic composition containing this novel extract, and also a cosmetic care method using this composition. The invention also provides a dermatological composition containing this novel extract.

Finally, the purpose of the invention is to solve all the technical problems by means of a simple, relatively inexpensive solution that can be used on an industrial scale, in particular in the cosmetics industry.

DESCRIPTION OF THE INVENTION

Thus, according to a first subject, the invention relates to an extract of the seeds of the *Kniphofia uvaria* plant. This extract can be obtained by bringing said seeds into contact with at least one nonpolar solvent, preferably a cosmetically or dermatologically acceptable solvent, or else by mechanical pressing of said seeds.

The term "nonpolar solvent" is intended to mean a compound in the liquid state, the dipolar moment of which is zero, either due to the absence in its molecular structure of polar groups forming an electric dipole, or owing to its molecular geometry which means that, in the presence of polar groups, the dipolar moments cancel each other out.

The seed extract is preferably a lipophilic extract. The term "lipophilic extract" is intended to mean an extract obtained by bringing the seeds into contact with a nonpolar solvent or by a mechanical pressing of the seeds. According to one preferred embodiment, the seed extract is an oil that is liquid at ambient temperature (25° C.).

Prior to the solvent extraction step or prior to the mechanical pressing, the seeds harvested may have been dried and/or ground.

The nonpolar solvent that can be used in such an extraction process may be advantageously chosen from carbon dioxide ($CO_2$) and cosmetically or dermatologically acceptable linear, branched or cyclic saturated alkanes, which are unsubstituted or substituted with one or more chlorine atoms, advantageously $C_6$ or $C_7$ alkanes.

A subject of the invention is also a lipophilic plant extract of the *Kniphofia uvaria* plant obtained by means of an extraction process in which the extraction solvent is carbon dioxide in the subcritical or supercritical state. The part of the plant used is preferably the seeds.

The supercritical state of a fluid is defined as being the state of this fluid when it is subjected to temperature and pressure conditions such that the temperature applied is above a critical temperature (Tc) and the pressure applied is above a critical pressure (Pc), these critical values being specific to each fluid.

For carbon dioxide, the critical temperature Tc is equal to 31° C. and the critical pressure Pc is equal to $7.38 \times 10^6$ Pa.

According to one embodiment, the carbon dioxide is in the supercritical state at a temperature ranging from 35° C. to 80° C., and a pressure above $7.4 \times 10^6$ Pa.

The subcritical state is defined as being the state of a fluid when the temperature to which it is subjected is below the critical temperature (Tc) (Tc=31° C. for carbon dioxide), it being possible for the pressure to then be, unimportantly, below or above the critical pressure (Pc=$7.38 \times 10^6$ Pa for carbon dioxide).

The temperature and pressure conditions are adjusted so as to place the carbon dioxide in the desired state; however, the pressure may represent a value ranging up to 300 times atmospheric pressure (1 atm=$0.101 \times 10^6$ Pa), but a pressure of between $8 \times 10^6$ Pa and $30 \times 10^6$ Pa is preferentially used for an extraction with carbon dioxide in the supercritical state, and a pressure of between $6.5 \times 10^6$ Pa and $10 \times 10^6$ Pa is preferentially used for an extraction in the subcritical state.

Advantageously, the carbon dioxide is compressed at a pressure above $7.4 \times 10^6$ Pa, preferably above or equal to $18 \times 10^6$ Pa and particularly preferably above or equal to $25 \times 10^6$ Pa.

More advantageously, the extraction is carried out at a temperature between 35° C. and 80° C.

Preferentially, said extraction is an extraction with carbon dioxide in the supercritical state.

As optional and/or additional means in such an extraction process, use may be made of organic solvents as cosolvent or an entrainment agent, for modifying the polarity of the mixture formed with the carbon dioxide, reinforcing the solvent capacity with respect to certain molecules which are barely soluble or insoluble in carbon dioxide in the supercritical or subcritical state and/or for facilitating the entrainment of the mixture formed.

By way of example, mention is made of ethanol as cosolvent that can be used for modifying the polarity of the mixture formed with the carbon dioxide, or else fatty acid esters such as, for example, dicaprylyl carbonate (Cetiol CC®, Cognis GmbH), cetearyl isononanoate (Cetiol SN®, Cognis GmbH) or else caprylic/capric triglyceride (Mygliol 812®, Hüls AG), that can be used as entrainment agent.

When one of these solvents is used during the extraction process, its concentration is advantageously less than or equal to 5% by weight relative to the weight of carbon dioxide used for the extraction.

At the end of the actual extraction step, a phase of expansion by lowering the pressure and optionally the temperature causes the carbon dioxide to go from the subcritical or supercritical state to the gaseous state, thereby making it possible to completely remove the carbon dioxide from the extract obtained. The organic solvent optionally used as entrainment agent or cosolvent is also removed during this step.

The extraction process may also be completed by a step of partial or total removal of the extraction solvents.

This drying step preferentially consists of an operation in which the extract obtained is lyophilized or a heating step, advantageously under vacuum.

In order to improve the organoleptic aspect of the extract, the process for obtaining the extract may also advantageously comprise a deodorizing and/or decoloring step, by steam distillation, by molecular distillation or by decoloring with active carbon.

A preferred extract is obtained by bringing seeds of the *Kniphofia uvaria* plant into contact with carbon dioxide in the subcritical or supercritical state, preferably in the absence of cosolvent.

According to one preferred embodiment, pre-dried seeds are used.

According to one embodiment, the extraction is carried out at a temperature ranging from 35° C. to 80° C. and particularly preferably 60° C. Advantageously, the extraction of the seeds of the plant is carried out at the temperature of 60° C. and at the pressure of 290 bar ($29 \times 10^6$ Pa).

According to one alternative of the extraction process using a nonpolar solvent, the extract of the invention can be obtained by subjecting the seeds of the plant to mechanical pressing. This pressing is advantageously carried out under cold conditions, preferably on the unground seeds, which may have been pre-dried.

Another subject of the invention relates to the use of a plant extract of the seeds of the *Kniphofia uvaria* plant, preferably an oil extract of the seeds, as an active agent and/or excipient in a cosmetic or dermatological composition.

This extract is particularly suitable for cosmetic use, in particular in cosmetic compositions comprising at least one fatty phase. Its consistency makes it of greater interest for use as an excipient in cosmetic compositions, in particular in those comprising at least one fatty phase or consisting of a fatty phase.

According to a second subject, the invention relates to a cosmetic or dermatological composition comprising the extract previously described and at least one cosmetically or dermatologically acceptable excipient.

The composition preferably comprises an effective amount of the extract for obtaining the desired effect. The composition thus preferentially comprises from 0.0001% to 10% by dry weight of extract, preferably from 0.01% to 5% by weight, relative to the total weight of the composition.

The percentages by dry weight are expressed on the basis of the weight of the extract not comprising extraction solvent or comprising the latter in trace amounts.

By way of example, the lipophilic plant extract may be contained in the fatty phase of oil-in-water emulsions, such as skin care creams, or in fatty phases of makeup compositions, such as lipsticks or mascaras.

These compositions may comprise an aqueous phase or else be substantially anhydrous, i.e. contain only traces of residual water.

The extract of the invention may also be combined, in cosmetic or dermatological compositions, with other cosmetically acceptable active agents, in the form of purified molecules and/or of extracts, in particular of plant extracts, having cosmetic effects similar and/or complementary to those of said extract of the invention.

Such active agents may be chosen from substances having a skin lightening activity; substances having a slimming activity; substances having a moisturizing activity; substances having a calming, soothing, or relaxing activity; substances having skin microcirculation-stimulating activity for improving the radiance of the complexion, in particular of the face; substances having a sebum-regulating activity for oily skin care; substances intended for cleansing or purifying the skin; substances having a free-radical-scavenging activity; substances intended for reducing or delaying the effects of skin aging, in particular the formation of wrinkles, by means of an activity aimed at promoting the maintaining of the structure of the skin and/or limiting the degradation of the extracellular matrix of the superficial layers of the dermis and of the epidermis and/or obtaining a protective, correcting or restructuring effect on the skin; substances having an anti-inflammatory activity.

Advantageously, the composition of the invention also comprises at least one cosmetically or dermatologically acceptable excipient which may be chosen from pigments, dyes, polymers, surfactants, rheology agents, fragrances, electrolytes, pH adjusters, antioxidants, preservatives, and any mixture thereof.

The composition may be, for example, a serum, a lotion, a cream, an oil-in-water emulsion, a hydrogel, a mask or an oil-in-water emulsion, or else be in the form of a stick, a patch, or a makeup product of lipstick, mascara or foundation type.

The extract and the composition of the invention exhibit an effect which is particularly desired for preventing or delaying the appearance of the signs of skin aging or for slowing down or reducing the effects thereof.

A third subject of the invention is thus directed toward the use, in a cosmetic or dermatological composition, of at least one plant extract of the invention:

as an agent intended for preventing or delaying the appearance of the signs of skin aging, in particular caused or accelerated by UV rays, and/or as an anti-inflammatory agent, and/or as an agent for improving the elasticity or the firmness of the skin, and/or as a moisturizing agent.

The cosmetic or dermatological composition is advantageously as previously defined.

The extract may also be used in a cosmetic or dermatological composition:

as an agent for inhibiting the secretion of metalloproteinases and of Pro-MMP1, and/or as a peroxisome proliferator-activated receptor (PPAR) agonist.

The extract may further be used in a cosmetic or dermatological composition:

as an agent for preserving the extracellular matrix against degradation, in particular accelerated by UV radiation, as an agent for reinforcing the horny layer, in particular by stimulating the synthesis of epidermal lipids, as an agent for limiting the process of chronic inflammation harmful to the skin associated with secretions of cells stressed by endogenous free radicals or free radicals produced by UV radiation, and/or senescent cells, as an agent for treating skin disorders, in particular problems of dryness of the skin, possibly associated with aging, which involve a reduction in the production of lipids which contributes to the disruption of the barrier function of the skin, as an agent for soothing skin which is irritated, for example under the effect of UV radiation or of the use of alpha-hydroxy acids, in particular during exfoliation or a peel.

Finally, a fourth subject of the invention is directed toward a cosmetic care method comprising the application, to at least one part of the skin of the face or of the body exhibiting signs of aging, such as wrinkles or slackening, of an effective amount of a composition or of an extract as previously defined, for slowing down skin aging or reducing the effects thereof.

A subject of the invention is also a composition for use in the treatment of the cutaneous reactivity of sensitive skin and/or the irritation of the skin of a patient.

The invention also relates to a dermatological composition as previously described, for use in the treatment of the signs of intrinsic or extrinsic aging of the skin, and/or in the treatment of the process of chronic inflammation harmful to the skin associated with secretions by stressed and/or senescent cells.

Advantageously, the cosmetic or dermatological composition is applied to an area of skin of the body or of the face exhibiting visible signs of aging, such as the presence of wrinkles or of fine lines, an irritation, inflammatory signs, a loss of radiance of the complexion, a loss of firmness and/or of elasticity of the skin or other signs, such as a decrease in the thickness of the skin, or an increase in the dryness or in the roughness of the skin.

Advantageously, the cosmetic composition is applied to an area of skin of the body or of the face exhibiting no visible signs of discomfort or of sensitivity.

Other purposes, characteristics and advantages of the invention will become more clearly apparent in the light of the explanatory description which follows, given with reference to examples of extract preparation and of tests demonstrating the properties of the extract and to examples of a cosmetic composition using such an extract, which are given by way of illustration of the invention without, however, limiting the scope thereof.

In the examples, all the percentages are given by weight, the temperature is in degrees Celsius, and the pressure is atmospheric pressure, unless otherwise indicated.

EXAMPLES

Example 1

Preparation of an Extract of *Kniphofia uvaria* Seeds

Preparation of Extracts of the Invention Using a Nonpolar Solvent

The seeds, collected from the plants of the *Kniphofia uvaria* species, were dried and then ground.

The plant matter resulting from this grinding was extracted using $CO_2$ in the supercritical state, in the absence of cosolvent.

The conditions of the extraction process were the following:

pressure=$29 \times 10^6$ Pa (290 bar)/temperature=60° C. (under these pressure and temperature conditions, the carbon dioxide is in the supercritical state).

The extract obtained was dried by distillation with a rotary evaporator, under vacuum, at 50° C., in the presence of ethanol (5% by weight relative to the extract).

The extract obtained (EXTRACT 1) after drying was a clear, orange-colored oil. The extraction yield was 25% by weight relative to the plant matter used.

Preparation of Extracts of the Invention by Cold Pressing

Pre-dried whole seeds are mechanically cold-pressed using a press suitable for this purpose.

The oil collected is filtered.

It is subjected to a steam deodorization step, in order to improve the organoleptic properties thereof.

In the examples hereinafter, the term "extract" used alone refers to the extract of the invention prepared in accordance with the present example by one or other of the means described.

Example 2

In Vitro Tests for Activity of an Extract of the Invention

1) MMP-2, MMP-9, pro-MMP-1 Markers 1.1) Biological Activities

Prior to the treatment, a stock solution of the extract of example 1, dissolved in DMSO at the concentration of 6.25 and 12.5 mg of extract per ml of solvent, or of the controls, was prepared.

At the time of the treatment of the cells with the extract of the invention, the stock solution is diluted to $\frac{1}{1000}^{th}$ in the culture medium so as to achieve the desired concentration.

An extract of *Anogeissus leiocarpus* and resveratrol, the capacity of which to inhibit the synthesis of these proteins by fibroblasts in culture is known, are used as positive controls.

The tests are carried out on normal human fibroblasts (NHFs).

The NHFs are seeded at the density of 5000 cell/well and 200 μl/well of MEM culture medium (Gibco Invitrogen) supplemented with glutamine (Gibco Invitrogen, final concentration 2 mM) and 10% of FCS (fetal calf serum), in a 96-well microplate (Flacon). The culture plate is placed in an incubator for 24 hours in order to obtain 80% cell confluence.

The cells are treated with *Anogeissus leiocarpus* at 25 μg/ml and a solvent control (DMSO). A UV-B control is also prepared by subjecting the fibroblasts to UV-B radiation, so as to validate the stimulation of the secretion of MMPs by the cells under the influence of this factor.

The extract at various concentrations, the positive control and the solvent control are each evaluated on 4 wells of NHFs.

After 48 hours of treatment, the culture supernatants are removed and stored at −20° C. The sandwich immunoenzymatic technique, which makes it possible to assay in the supernatants, by spectrophotometric measurement at 450 nm, the respective amounts of MMP-2, MMP-9 and pro-MMP-1, is used. The MMP-2, MMP-9 and pro-MMP-1 assays are carried out according to the protocols described in the Quantikine kits (R&D Systems).

1.2) Results

The results are given in the tables below.

TABLE 1

| MMP-9 assay | | | | | |
|---|---|---|---|---|---|
| | T DMSO | T + UVB | T+ | EXTRACT 1 | EXTRACT 1 |
| Dose (μg/ml) | | | | 6.25 | 12.5 |
| mean (ng MMP-9/μg prot) | 0.0202 | 0.0539 | 0.0251 | 0.0449 | 0.0369 |
| Standard deviation | 0.0005 | 0.0017 | 0.0010 | 0.0046 | 0.0003 |
| % inhibition | | | 53.46 | 16.73 | 31.52 |

Table Legends:
T DMSO = dissolution solvent control (DMSO),
T + UVB = positive control for stimulation with UVB radiation producing an increase in MMP-9 level
T+ = positive control for the test (anogelline).

TABLE 2

| MMP-2 assay | | | | |
|---|---|---|---|---|
| | T DMSO | T+ | 12.5 μg/ml | 6.25 μg/ml |
| mean (ng MMP-2/μg prot) | 0.1437 | 0.0416 | 0.1281 | 0.1215 |
| % inhibition | | 71.07 | 10.86 | 15.44 |

TABLE 3

| pro-MMP-1 assay | | | | |
|---|---|---|---|---|
| | T DMSO | T + UVB | T+ | 12.5 μg/ml |
| mean (ng MMP1/μg prot) | 0.0196 | 0.0291 | 0.0137 | 0.0017 |
| % inhibition | | | 52.8 | 94.1 |

1.2) Conclusions

MMP-2 is expressed by fibroblasts during tissue development and regeneration. With MMP-9, this protein degrades type IV collagen, which is a major compound of basal membranes and of gelatin (denaturated collagen). It can also degrade other collagen types (V, VII and X) like elastin and fibronectin. The substrates for MMP-9 can be native type IV, V, VII, X and XI collagens, and fibronectin. MMP-1 is a major enzyme involved in extracellular matrix degradation. Unlike MMP-2, the production of MMP-1 is governed by the AP-1 transcription factor which is directly influenced by environmental stresses, such as UV radiation, which accelerates skin aging.

Treatment of the cells with a solution of the extract of *Kniphofia uvaria* seeds made it possible to significantly inhibit the secretion of metalloproteinases and of pro-MMP-1.

Owing to this activity of the extract of the invention, it is advantageous to use it in cosmetic compositions for limiting the effects of skin aging, in particular caused or accelerated by UV rays, and thus contributing to limiting the process of chronic inflammation harmful to the tissue associated with secretions by stressed and/or senescent cells.

2) PPAR Ligand 2.1) Protocol

The test was carried out on a stable transfected cell line (Seimandi et al., Analytical Biochemistry, 2005, 344, 8-15)

possessing a PPARβ/δ reporter system, expressing a chimeric protein containing the ligand-binding domain of human PPARβ/δ fused with the DNA-binding domain of the yeast transcription factor GAL-4 (DBD).

The luciferase reporter gene was under the control of a pentamer of the GAL-4 recognition sequence located in front of the β-globulin promoter (Normand et al., *Proceedings MipTec—The 9th International Conference and Exhibition on Drug Discovery, Aug.* 5, 2006-Nov. 5, 2006, P 105).

The compounds were tested in 96-well plates in which the cells were seeded. They were incubated for 24 hours with the active agent tested. The cells were brought to confluence greater than 80%. The extract of example 1 was dissolved in DMSO and then diluted in the culture medium so as to achieve the desired concentration. The luciferase activity was measured by luminescence. The selectivity of compounds for PPAR receptors is determined by comparison with a reference and of a negative control (0.1% DMSO).

In order to determine the activity of the extract of the invention on the PPAR receptor subtypes, the activity of the luciferase was monitored by luminescence corresponding to the activation of PPARβ/δ. The values obtained were expressed as % luciferase activity of the ligand tested compared with the activity of a reference pharmacological agonist bound at 100% (L16541 1 µM, TEBU-BIO).

2.2) Results

For the *Kniphofia uvaria* extract of example 1, the test gave the activity values below:

- at 10 µg/ml in the culture medium: the response represents 14% of the effect of the positive control (100% agonist),
- at 30 µg/ml in the culture medium: the response represents 37% of the effect of the positive control,
- at 50 µg/ml in the culture medium: the response represents 43% of the effect of the positive control (100% agonist).

2.3) Conclusions

Peroxisome proliferator-activated receptors (PPARs) are transcription factors which belong to the nuclear receptor superfamily. PPARs bind to a specific region of DNA located in the regulatory region of target genes, mainly involved in lipid metabolism. PPARβ/δ represents the predominant isotype in human epidermis, with a high level in keratinocytes (Girroir et al, *Biochem. Biophys. Res. Comm.,* 2008, 371, 456-461).

As explained in the introductory part, PPARs play an essential role in the physiology of the epidermis, in particular with respect to its barrier function quality, and to its regulatory role with regard to the inflammatory status, and it is thus very advantageous to identify agonists of these receptors.

*Kniphofia* oil is a powerful PPARβ/δ agonist of plant origin, with a dose-dependent effect.

This activity with respect to PPAR receptors makes this extract usable in the cosmetics industry in applications aimed at treating skin disorders, in particular problem of dryness of the skin, possibly associated with aging, which involve a decrease in lipid production which contributes to the disruption of the barrier function of the skin (Ghadially R. et al, *J. Gin. Invest.,* 1995, 95, 2281-2290, Seyfarth F et al., *Clinics Dermatol.,* 2011, 29, 31-36).

The anti-inflammatory potential of this extract, which is a PPARβ/δ antagonist, makes it possible to also envision its use as an active agent, in particular for modulating the cutaneous reactivity of sensitive skin, for soothing skin which has been irritated, for example, under the effect of UV radiation, or else for limiting the harmful cycle of chronic micro-inflammation which senescent cells initiate in aged skin.

Example 3

Effect of the Treatment of Normal Human Fibroblasts with the Extract of the Invention on Gene Expression The purpose of this study was to study the biological activity of an extract of the invention on the expression of genes encoding proteins involved in biological processes associated with skin aging or the moisturization state of the skin, on a culture of normal human fibroblasts (NHFs) cultured in monolayer.

The TLDA technology, TLDA standing for Taqman Low density Array, makes it possible to study the modulation of the expression of a panel of genes, encoding proteins specific for biological pathways associated with fibroblasts, in response to a treatment lasting 24 h with the extract obtained in example 1 (EXTRACT 1).

1. Materials and Methods

Cell Culture

Normal human fibroblasts (NHFs), from a Caucasian adult donor, were seeded in 6-well plates in a proportion of $2.5 \times 10^4$ cells/well in medium 1 having the composition below:

| Medium 1 | | |
|---|---|---|
| | Supplier | Final concentration |
| FCS | Biowest | 10% |
| DMEM | Fisher | qs |

Three wells of NHFs were seeded per culture condition. 24 hours before the treatment, at confluence, the cells were depleted of fetal calf serum (medium 2) with the composition below:

| Medium 2 | |
|---|---|
| | Supplier |
| DMEM | Fisher |

2. Treatment

After 24 hours of culture without fetal calf serum, the cells were treated with EXTRACT 1 of the invention, at 0.1% by weight in medium 2. After 24 hours of treatment, the cells were recovered to extract the total RNA therefrom.

A nontreated control was also carried out under the same conditions.

3. PCR Taqman Low Density Array 3.1 Obtaining of Total RNA

The cell culture medium was removed, and 250 µl of lysis buffer RLT (supplied in the Nucleospin RNA trace kit) were added. The cells were scraped using a cell scraper and then the cell lysis was recovered in a 1.2 ml deepwell (supplied in the kit). The total RNA was extracted using an Epimotion 5075 (Eppendorf) with the Nucleospin RNA trace kit (Macherey Nagel).

The total RNA solutions obtained were assayed and their quality was verified using the bioanalyzer 2100 (Agilent Technologies). This apparatus was connected to a computer having the specific result analysis software (2100 expert software). The technique required a 12-well microplate (RNA 6000 NanoChips) and a kit of reagents (RNA 6000 Nano Reagents & Supplies) specific for the assaying of eukaryotic total RNA.

3.2 Synthesis of Complementary DNAs

The reverse transcription (RT) kit used was the high capacity cDNA Reverse Transcription Kit (Applied Biosytems). 100 ng of total RNA were diluted in water for a final volume of 50 µl. They were then incubated for 10 minutes at 25° C. and then for 2 hours at 37° C. with 50 µl of 2× high capacity reverse transcription kit reaction mix prepared beforehand as indicated below.

| Reactives | volume |
|---|---|
| RT buffer | 10 µl |
| dNTP buffer | 4 µl |
| Random primer | 10 µl |
| RNAse out | 1 µl |
| RT | 5 µl |
| H$_2$O | 20 µl |

3.3 PCR Taqman Low Density Array

50 µl of each RT were sampled and mixed with 50 µl of "Taqman Gene Expression master mix". After homogenization, the 100 µl were deposited on microfluidic cards, and the latter were centrifuged and then sealed.

Control genes were used to standardize the results. The PCR was carried out according to the protocol supplied by Applied Biosystems, in the ABI Prism 7900HT Sequence detection system apparatus. The qPCR steps were 2 min at 50° C., 10 min at 94.5° C., then 30 s at 97° C. and 1 min at 59.7° C. for 40 cycles.

3.4 Analysis of the Results

In the RT-PCR TLDA method, the quantification is carried out using the ΔCt comparative method. This method determines the number of cycles (Ct) of each gene of the card using the RQ Manager software which takes into account the background noise for each gene. This number of cycles (Ct) was standardized with respect to the Ct of a housekeeping gene, GAPDH, which does not vary in the cells.

4. Results

The analysis carried out on various genes involved in processes associated with the skin aging, with moisturization of the skin or with the maintaining of its elasticity and of its firmness were studied using the method described below.

Metalloproteinase 1 (MMP-1)

Metalloproteinase 1 (MMP-1) acts in the degradation of collagens and more particularly of collagens 1 and 3. It is particularly induced during skin aging and in response to UV exposure. It is therefore strategic to want to inhibit the expression of this protein, so as to control the degradation of the dermal extracellular matrix. The results obtained demonstrate that the treatment of NHFs with the extract of the invention makes it possible to significantly reduce (−84%) the expression of MMP-1 after 24 hours of treatment, compared with the control.

The effect of the extract of the invention on the expression of this metalloproteinase is particularly advantageous for preventing or slowing down skin aging, by limiting ECM degradation.

Low Density Protein Receptor Related Protein-1 (LRP-1).

The treatment of NHFs with the extract of the invention makes it possible to significantly increase (+190%) the expression of the protein encoded by the LRP-1 gene compared with the control.

This LRP-1 gene encodes an LDL receptor, described as having an action in the "endocytosis" of excess MMPs in the pericellular space.

The effect of the extract of the invention on the expression of this gene is therefore particularly advantageous for preventing or slowing down skin aging, by acting positively on ECM degradation.

Elastin (ELN)

The treatment of NHFs with the extract of the invention makes it possible to significantly increase (+135%) the expression of tropoelastin encoded by the ELN gene compared with the control.

The effect of the extract of the invention on the expression of this gene is therefore particularly advantageous for preventing or slowing down skin aging, by acting positively on elastin synthesis.

Collagen 1A1

The treatment with the extract of the invention makes it possible to significantly increase (+103%) the expression of collagen 1A1 by stimulation of the COL A1A gene.

The effect of the extract of the invention on the expression of this gene is therefore particularly advantageous for preventing or slowing down skin aging, by acting positively on collagen synthesis in the extracellular matrix.

Example 4

Effect of the Treatment of Normal Human Keratinocytes with the Extract of the Invention on Gene Expression The objective of this study was to evaluate the effect of an extract of the invention on the expression of genes encoding proteins involved in processes associated with aging or with moisturization of the skin.

1. Cell Culture

Normal human keratinocytes (NHKs) from a Caucasian adult donor were seeded in 6-well plates in a proportion of 2.5×10$^4$ cells/well in medium 1. Three wells of NHKs were seeded per culture condition, for a treatment of 8 hours.

2. Treatment

At 80% confluence, the cells were treated with the extract of the invention of example 1, at 0.1% by weight in medium 1 below:

| | Supplier |
|---|---|
| Epilife | Fisher |
| Supplements | Fisher |

After 24 hours of treatment, the cells were recovered in order to extract the total RNA therefrom.

3. PCR Taqman Low Density Array

The protocol is identical to that described in the previous example.

4. Results

As in the previous example, the analysis is carried out on genes involved in the expression of proteins involved in processes associated with skin aging, with moisturization of the skin or with the maintaining of its elasticity and of its firmness.

TIM P-2

The results obtained demonstrate that the treatment of NHKs with the extract of the invention makes it possible to significantly increase (+30%) the expression of proteins which inhibit metalloproteinase type 2, after 24 hours of treatment, compared with the control.

This protein essentially inhibits the metalloproteinases MMP-2 and MMP-9. The effect of the extract of the invention on the expression of this metalloproteinase is particularly advantageous for preventing or slowing down skin aging, by limiting the degradation of the elastic fibers of the extracellular matrix (ECM).

Collagen 4A1

The results obtained demonstrate that the treatment of NHKs with the extract of the invention makes it possible to significantly increase (+39%) the expression of type 4 collagen. This collagen plays a fundamental role in maintaining the integrity of the dermoepidermal junction.

The effect of the extract of the invention on the expression of this collagen is particularly advantageous for maintaining the integrity of the extracellular matrix (ECM) and thus combating the effects of skin aging.

Aquaporin-3

The results obtained demonstrate that the treatment of NHKs with the extract of the invention makes it possible to significantly increase (+160%) the expression of aquaporin type 3. This collagen plays a fundamental role in maintaining the integrity of the dermo-epidermal junction.

The effect of the extract of the invention on the expression of this aquaporin in keratinocytes makes it possible to promote transfers of cell water and improves the moisturization state of the superficial layers of the skin.

Hyaluronan Synthase-3

The results obtained demonstrate that the treatment of NHKs with the extract of the invention makes it possible to significantly increase (+240%) the expression of the protein encoded by the HAS3 gene. This enzyme is involved in the synthesis of hyaluronic acid, which plays an important role in maintaining the moisturization state of skin cells.

CD-44

The results obtained demonstrate that the treatment of NHKs with the extract of the invention makes it possible to significantly increase (+45%) the expression of this hyaluronic acid receptor. This significant effect makes it possible to improve or maintain the moisturization state of skin cells treated with an extract of the invention.

Example 5

Face Cream

The extract of *Kniphofia uvaria* seeds was obtained by reproducing the process of example 1. An additional step of deodorization by steam distillation was also carried out on EXTRACT 1 so as to improve the organoleptic characteristics of the extract used in the cosmetic composition below.

A solution of extract was used as an active agent for the preparation of the cosmetic composition below (% expressed by weight relative to the final composition):

Phase A

| | |
|---|---|
| Phenoxyethanol | 0.5 |
| Xanthan gum | 0.2 |
| Acrylate/C20-30 alkyl acrylate cross polymers | 0.2 |
| Tetrasodium EDTA | 0.1 |
| Water | qs | qs: quantity sufficient to dissolve the compounds of phase A

Phase B

| | |
|---|---|
| *Kniphofia uvaria* extract according to the invention | 1 |
| Hydrogenated polyisobutene | 4 |
| Squalane | 3 |
| Caprylic/capric triglycerides | 3 |
| Pentylene glycol | 3 |
| Glyceryl stearate | 3 |
| PEG-100 stearate | 2.5 |
| Beeswax | 1.5 |
| Dicaprylyl carbonate | 1.5 |
| Cetyl alcohol | 1 |
| Stearyl alcohol | 1 |
| Dimethicone | 1 |

Phase C

| | |
|---|---|
| Sodium hydroxide | 0.04 |
| Water | qs 100 | qs 100: quantity sufficient for 100% of the final composition

The excipients of phase A were dispersed in water, then the mixture was heated to 80° C.

The compounds of phase B, including the *Kniphofia uvaria* extract, were heated to 85° C. in order to form a homogeneous phase.

Phase B was emulsified in phase A using a Ystral mixer.

The resulting oil-in-water emulsion was finally neutralized with an aqueous 0.04% w/w sodium hydroxide solution (phase C), and then cooled.

The composition obtained can be used as a cream intended to be applied to all or part of the face.

This cream makes it possible to obtain an effect of preventing or slowing down skin aging, but also produces a soothing effect on the skin with respect to entities that produce an inflammatory effect on the skin.

The formula is reproduced while replacing EXTRACT 1 with EXTRACT 2 obtained by pressing. The composition has the same appearance as that prepared above.

The invention claimed is:

1. A cosmetic or dermatological composition, comprising:
   from 0.0001% to 10% by dry weight of an extract of *Kniphofia* uvaria seeds that is obtained by bringing the *Kniphofia* uvaria seeds into contact with carbon dioxide in a supercritical state having a temperature ranging from 35° C. to 80° C. and a pressure above $7.4 \times 10^6$ Pa and removing said carbon dioxide, and
   at least one cosmetically or dermatologically acceptable excipient selected from the group consisting of pigments, dyes, polymers, surfactants, rheology agents, fragrances, pH adjusters, antioxidants, preservatives, and any mixture thereof, and
   where the composition is formulated as a lotion, a cream, an oil-in-water emulsion, a hydrogel, a mask, a stick, a patch, a lipstick, a mascara, or a makeup type foundation.

2. The cosmetic or dermatological composition of claim 1, comprising from 0.01% to 5% by dry weight of the extract, relative to the total weight of the composition.

3. The cosmetic or dermatological composition of claim 1, for use
   as an agent intended for preventing or delaying the appearance of the signs of skin aging,
   as an anti-inflammatory agent,
   as an agent for improving the elasticity or the firmness of the skin, or
   as a moisturizing agent.

4. The cosmetic or dermatological composition of claim 1, for use
- as an agent for inhibiting the secretion of metalloproteinases and of Pro-MMP1,
  or
- as a peroxisome proliferator-activated receptor (PPAR) agonist.

5. The cosmetic or dermatological composition of claim 1, for use
- as an agent for preserving the extracellular matrix against degradation,
- as an agent for reinforcing the horny layer by stimulating the synthesis of epidermal lipids,
- as an agent for limiting the process of chronic inflammation harmful to the skin associated with secretions of cells that are stressed by endogenous free radicals or by free radicals produced by UV radiation,
- as an agent for treating dryness which involves a reduction in the production of lipids and contributes to the disruption of barrier function of the skin, or
- as an agent for soothing skin which is irritated by UV radiation or by the use of alpha-hydroxy acids.

6. A cosmetic care method for slowing down skin aging or reducing the effects thereof, said method comprising a step of applying to at least one part of a person's skin exhibiting signs of aging, an effective amount of a composition as defined in claim 1.

* * * * *